United States Patent [19]

Peet et al.

[11] Patent Number: 4,567,193

[45] Date of Patent: Jan. 28, 1986

[54] 2-(FORMYLAMINO)-N-(1H-TETRAZOL-5-YL)BENZAMIDE AND USE AS ANTI-ALLERGICS

[75] Inventors: Norton P. Peet; Shyam Sunder, both of Indianapolis, Ind.

[73] Assignee: Merrell Dow Pharmaceuticals Inc., Cincinnati, Ohio

[21] Appl. No.: 517,086

[22] Filed: Jul. 22, 1983

[51] Int. Cl.[4] .................... A61K 31/41; C07D 257/06
[52] U.S. Cl. .................................... 514/381; 548/251
[58] Field of Search ........................ 548/251; 424/269; 514/381

[56] References Cited

U.S. PATENT DOCUMENTS 4,146,631 3/1979 Ford et al. .................... 548/251

OTHER PUBLICATIONS

Vlietstra et al., Chem. Abstr., 97, Abst. No. 109524c, (1982).

Primary Examiner—Glennon H. Hollrah
Assistant Examiner—D. B. Springer
Attorney, Agent, or Firm—John J. Kolano

[57] ABSTRACT

2-(Formylamino)-N-(1H-tetrazol-5-yl)benzamide and its pharmaceutically acceptable salts are useful as antiallergic agents. The compounds are prepared by the reaction of 2-amino-N-(1H-tetrazol-5-yl)benzamide with formic acetic anhydride.

3 Claims, No Drawings

2-(FORMYLAMINO)-N-(1H-TETRAZOL-5-YL)BENZAMIDE AND USE AS ANTI-ALLERGICS

The present invention is directed to the formyl derivatives of 2-amino-N-(1H-tetrazol-5-yl)benzamide. More particularly, it is directed to the compound having the following structural formula:

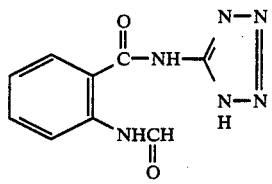

and the pharmaceutically acceptable salts thereof.

Equivalent for the purposes of this invention are the pharmaceutically acceptable salts and also the hydrates of the compounds and their salts. The term "pharmaceutically acceptable salts" as used herein, is intended to include non-toxic cationic salts such as the alkali metal salts, e.g., sodium and potassium; alkaline earth metal salts such as calcium, magnesium or barium; salts with ammonia; and salts with organic bases, e.g., amines such as triethylamine, n-propylamine and tri-n-butylamine.

The compounds of the present invention are prepared by the reaction of 2-amino-N-(1H-tetrazol-5-yl)benzamide with formic acetic anhydride in an inert solvent. The desired formamide forms readily and can be isolated from the reaction mixture by standard procedures.

The 2-aminobenzamide used as the starting material in the above process is obtained by catalytic hydrogenation of an alkaline solution of the corresponding 2-nitrobenzamide. The preferred catalyst is 5% Pd/C although similar catalysts, such as Pt/C, can also be used. The starting tetrazole is preferably dissolved in aqueous 1 N sodium hydroxide solution and, if necessary, this can be diluted with ethanol or additional water.

The necessary 2-nitrobenzamide is obtained by the reaction of the appropriate 2-nitrobenzoyl chloride with 5-aminotetrazole and the necessary acid chloride is obtained from the corresponding carboxylic acid, all using standard procedures.

The compounds obtained above are converted to the pharmaceutically acceptable salts by reacting the tetrazole final product with a substantially equimolar amount of the appropriate base in an aqueous solution or in a suitable organic solvent such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The compounds of the present invention possess antiallergic activity. Thus, they are useful in the treatment of conditions in mammals in which antigenantibody reactions are responsible for disease and particularly in the treatment of allergic diseases such as (but not limited to) extrinsic asthma, hay fever, urticaria, eczema or atopic dermatitis and upper respiratory conditions such as allergic rhinitis. The compounds of the present invention are particularly useful because they show prolonged activity. This activity is surprising in that the corresponding compounds without a formyl group on the 2-amino substituent exhibit activity of only short duration. That is, although the amino compound does show activity after administration, this activity falls off rather quickly so that the value of such a compound would be somewhat limited.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maizestarch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices administered by means of inhalers or other divices which permit the active compounds in the form of dry powders to come into direct contact with the lungs. The indicated compositions can be prepared by known techniques as described in standard texts such as *Remington's Pharmaceutical Sciences*, Mack Publishing Company, Easton, Pa.

The compounds of the present invention or pharmaceutical compositions thereof may be administered to human asthmatic patients in single oral doses of approximately 1-1000 mg of active ingredient and multiple oral doses totaling up to about 4000 mg/day of active ingredient. When administered by inhalation, lower doses are generally given, i.e., on the order of about one-tenth of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.

2. Animals—Adult male Sprague-Dawley or female Wistar Kyoto rats were used as antisera recipients in the test. The animals were allowed to acclimate for 5–14 days with food and water ad lib.

3. Sensitization—Recipient rats were passively sensitized by the intradermal injection of 100 microliters of two dilutions of antiserum (one injection on each side of the back). Sensitization occurred 48–72 hours prior to antigen challenge.

4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 240 minutes prior to challenge.

5. Antigen Challenge and Reaction Evaluation—Ovalbumin (0.1–1.0 mg in a 0.5% solution of Evan's Blue dye) in saline was given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both i.p. and orally.

In addition to activity in the PCA test as described above, the compounds of the present invention also inhibit the release of histamine in the rat Passive Peritoneal Anaphylaxis (PPA) test. This method can be described briefly as follows:

PPA Test Method

1. Antisera—Reaginic antibody to ovalbumin for this test was prepared in adult male $B_6D_2F_1$ mice.

2. Animals—Adult male Sprague Dawley or female Wistar Kyoto rats were used as antibody recipients. The animals were allowed to acclimate for 5–14 days with food and water ad lib.

3. Sensitization—Recipient rats were sensitized i.p. with 2 ml of an appropriate saline dilution of the mouse anti-ovalbumin antiserum determined from prior experiments. Sensitization took place 2 hours prior to antigen challenge.

4. Administration of Test Compound—Five to ten animals were used for each test compound/dilution. Compounds were homogenized in saline with an equivalent of sodium bicarbonate to effect solubilization, if appropriate, and administered i.p. at 60 μg, 30 seconds prior to antigen challenge or p.o. 5 to 60 minutes prior to antigen challenge.

5. Antigen Challenge and Assay Evaluation—Two mg of ovalbumin in 5 ml of modified Tyrode's Solution was administered by i.p. injection and the animals were sacrificed 5 minutes later. Peritoneal shock fluids were collected and classified by centrifugation. Protein was removed from the samples by perchloric acid precipitation and subsequent centrifugation. The samples were then analyzed for histamine content by an automated fluorometric assay. Histamine levels of peritoneal shock fluids from treatment animals were then compared to those of shock fluids from control animals. Drug effect was expressed as percent inhibition of histamine release.

The following examples are presented to illustrate the present invention but they should not be construed as limiting in any way.

EXAMPLE 1

To a solution of 10.3 g of 5-aminotetrazole monohydrate in 300 ml of tetahydrofuran and 15 ml of water was added 9.3 g of 2-nitrobenzoyl chloride. The solution was allowed to stand for 30 minutes before it was diluted with 200 ml of water and stored in a refrigerator for 72 hours. The solid which formed was separated by filtration to give 2-nitro-N-(1H-tetrazol-5-yl)benzamide melting at about 272°–273° C. with decomposition.

EXAMPLE 2

A solution was prepared from 19 g of 2-nitro-N-(1H-tetrazol-5-yl)benzamide in 100 ml of aqueous 1 N sodium hydroxide and 100 ml of ethanol. A 0.5-gram quantity of 5% Pd/C catalyst was added and the mixture was hydrogenated in a Parr apparatus at 1520 mm Hg pressure until uptake of hydrogen stopped. The catalyst was removed by filtration and the filtrate was treated with aqueous 1 N hydrochloric acid. The white solid which formed was separated by filtration and dried to give 2-amino-N-(1H-tetrazol-5-yl)benzamide melting at about 253°–254° C.

EXAMPLE 3

To a solution of 4.7 g of 2-amino-N-(1H-tetrazol-5-yl)benzamide in 30 ml of dimethylformamide, under nitrogen, was added 4.7 g of freshly prepared formic acetic anhydride. The precipitate which formed within a few minutes was separated by filtration and washed with ether to give 2-(formylamino)-N-(1H-tetrazol-5-yl)benzamide melting at about 247°–248° C. This compound has the following structural formula:

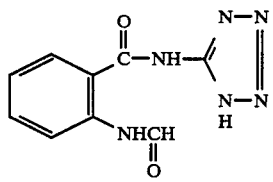

What is claimed is:

1. 2-(Formylamino)-N-(1H-tetrazol-5-yl)benzamide and the pharmaceutically acceptable salts thereof.

2. A compound according to claim 1 which is 2-(formylamino)-N-(1H-tetrazol-5-yl)benzamide.

3. A method for inhibiting the result of antibody-antigen reactions in mammals which comprises administration to a mammal susceptible to allergic reaction of an effective amount of 2-(formylamino)-N-(1H-tetrazol-5-yl)benzamide or a pharmaceutically acceptable salt thereof.